United States Patent [19]

Wood et al.

[11] Patent Number: 4,710,190

[45] Date of Patent: Dec. 1, 1987

[54] DIAPER HAVING IMPROVED REINFORCED AREA FOR RECEIVING ADHESIVE FASTENING TAPE

[75] Inventors: Leigh E. Wood, Woodbury; John A. Miller; Alan J. Sipinen, both of Maplewood, all of Minn.

[73] Assignee: Minnesota Mining and Manufacturing Company, St. Paul, Minn.

[21] Appl. No.: 903,680

[22] Filed: Sep. 4, 1986

[51] Int. Cl.$^4$ ............................................. A61F 13/16
[52] U.S. Cl. ..................................... 604/389; 604/390
[58] Field of Search ................................ 604/389, 390

[56] References Cited

U.S. PATENT DOCUMENTS

| | | |
|---|---|---|
| 2,714,889 | 8/1955 | Chambers . |
| 3,221,738 | 12/1965 | Ekberg et al. . |
| 3,867,940 | 2/1975 | Mesek et al. . |
| 4,210,144 | 7/1980 | Sarge, III et al. . |
| 4,296,750 | 10/1981 | Woon et al. . |
| 4,410,325 | 10/1983 | Lare ..................................... 604/389 |
| 4,523,334 | 6/1985 | Lavash ................................ 604/390 |
| 4,568,344 | 2/1986 | Suzuki et al. ....................... 604/389 |
| 4,576,598 | 3/1986 | Tritsch ................................ 604/389 |
| 4,643,730 | 2/1987 | Chen et al. ......................... 604/390 |

FOREIGN PATENT DOCUMENTS

| | | |
|---|---|---|
| 0080647 | 6/1983 | European Pat. Off. . |
| 3338201A1 | 10/1983 | Fed. Rep. of Germany . |
| 2114449 | 8/1983 | United Kingdom . |

*Primary Examiner*—John D. Yasko
*Attorney, Agent, or Firm*—Donald M. Sell; James A. Smith; Roger R. Tamte

[57] ABSTRACT

A disposable diaper is provided which includes an outer liquid-impermeable film and a bilayer film bonded to the liquid-impermeable film as a peel-resistant reinforced fastening area. The bilayer film comprises a reinforcing layer and a room-temperature-nontacky bonding layer. The bonding layer holding the reinforcing layer to the liquid-impermeable film with greater force than that which the fastening tape applies when adhered to the top of bilayer film.

19 Claims, 3 Drawing Figures

DIAPER HAVING IMPROVED REINFORCED AREA FOR RECEIVING ADHESIVE FASTENING TAPE

BACKGROUND

The present invention advances the art of disposable diapers that have a reinforced fastening area, i.e., an area of the diaper to which an adhesive tape is pressed and adhered to fasten the diaper around an infant or other person wearing the diaper. The fastening area generally lies along one side edge of the generally rectangular diaper, and lies on the outer liquid-impermeable film of the diaper, which in commercial disposable diapers is typically a thin film of polyethylene. The thinness of the polyethylene is desirable for several reasons, but when adhesive tape is adhered to it to fasten the diaper, or when the tape is removed to reposition the diaper or to check its condition, forces are applied that can tear the polyethylene and thus destroy the usefulness of the diaper.

The prior art has taught various techniques for reinforcing the outer impermeable film of the diaper. One technique involves coating the film with a reinforcing material either on the inner or outer surface of the film. See U.S. Pat. No. 4,296,750 (the interior surface of the outer impermeable film is coated with a hot-melt adhesive layer which has both a Ring and Ball softening point lower than that of the film and a modulus of elasticity lower than that of the film) or U.S. Pat. No. 4,210,144 (a hot-melt adhesive having high tensile strength and a low elongation to tensile force property relative to the outer impermeable film is applied on the outer impermeable film in a predetermined pattern, e.g., as an array of parallel stripes, preferably on the inner surface of the film to both bond the film to the absorbent pad of the diaper and to reinforce the film). Problems with this technique include the facts that the cohesive strength of the coating can be too low to allow lasting and complete holding of an adhesive tape pressed against it; some coating materials taught in the patents have a high softening point that can lead to deformation of polyethylene during coating; and patterned coatings can lead to nonuniform reinforcement.

A different technique of reinforcement involves adhering a plastic strip to the fastening area of the diaper. Teachings in the literature about this technique include U.S. Pat. No. 3,867,940 (a scrim or plastic film is bonded to the impermeable film "by known methods" or, if a polyethylene gauze is used, by heat and pressure); European Patent Application No. 0,080,647, published June 8, 1983 (a plastic strip such as a smooth-surfaced polypropylene strip is adhered to the impermeable film by a "layer of adhesive"); and German Offenlegungsschrift No. 33 38 201 A 1, laid open April 26, 1984 (a plastic strip of preferably polyethylene or polypropylene or polyester is "firmly adhered" to the impermeable film).

In commercial practice, the plastic strip of this technique has been adhered to the outer impermeable film with a pressure-sensitive adhesive. While offering convenient adhesion, the use of pressure-sensitive adhesives has a number of disadvantages. For example, to allow a uniform low-force unwinding of the adhesive-coated plastic reinforcing strip from a storage roll, the top surface of the reinforcing strip, i.e., the surface which becomes the target area to which the fastening tape is adhered in fastening the diaper around an infant, is typically covered with a low-adhesion backsize (LAB), thereby minimizing adhesion between the adhesive layer and that top surface. But the minimizing of adhesion to the target area where the fastening tape is to be adhered is exactly contrary to an intended characteristic of the target area, i.e., the characteristic of providing a surface to which the fastening tape can become reliably and lastingly adhered. An LAB could be avoided by covering the pressure-sensitive adhesive surface with a release liner, but such a liner adds undesired cost.

DISCLOSURE OF INVENTION

The present invention provides a new disposable diaper having a reinforced fastening area, but which avoids the use of low-adhesion backsizes, release liners, or other release treatments or agents; achieves economies of manufacture; and provides a durable fastening area to which adhesive fastening tapes may be aggressively adhered. A new diaper of the invention includes an outer liquid-impermeable film, generally of polyethylene, reinforced by bonding to it a bilayer film that comprises a reinforcing layer and a room-temperature-nontacky bonding layer, is free of release treatments on its top surface that provides the fastening area of the diaper, and is bondable to the liquid-impermeable film under heat and pressure that leaves the liquid-impermeable film substantially undeformed.

The bilayer film is based on and incorporates in the bonding layer what may be termed a high-cohesive-strength, narrow-softening-range "warm-melt adhesive", i.e., a composition that softens and bonds at comparatively low temperatures, e.g., less than about 115°–120 ° C., and preferably less than about 100° C.; has high cohesive strength beyond that available from waxes or other materials that soften at lower temperatures, such that it will lastingly hold a reinforcing layer in place; and is non-blocking, i.e., the bilayer film is windable into a storage roll in which, under normal storage conditions of about 50° or 60° C. or less, the overlying portions of bilayer film do not become adhered together so as to resist uniform low-force unwinding. The bilayer film becomes bonded to the liquid-impermeable film in a peel-resistant manner, such that aggressively adhesive fastening tapes may be strongly adhered to the fastening area by simple hand pressure and lastingly held to the diaper without cohesive or other failure of the reinforced portion of the diaper. Further, the fastening tapes may be removed and reapplied, all without distortion or tearing of the liquid-impermeable film or other damage to the diaper.

DETAILED DESCRIPTION

Figure 1:
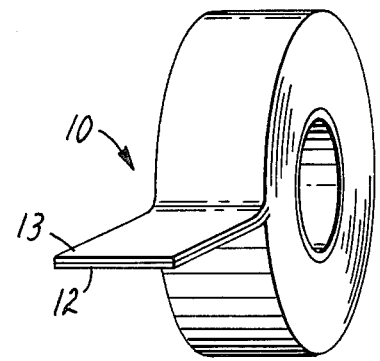
FIG. 1 is a perspective view of a roll of bilayer film of the invention.

A variety of materials can be used to provide the reinforcing layer of a bilayer film of the invention, i.e., the layer that provides the principal reinforcement to the outer impermeable film of a disposable diaper and provides a high-cohesive-strength adhesive-tape-receiving surface. The reinforcing layer should have a high strength, typically higher than that of the bonding layer, through use of high strength materials and/or through the use of greater thicknesses of materials. The reinforcing layer may be described as typically having a high absolute tensile strength, meaning that even if its tensile strength per unit of cross-sectional area is not higher than that of the liquid-impermeable film or the bonding layer, its absolute strength per unit of width rather than per unit of area is higher. However, the tensile strength of the reinforcing layer preferably exceeds 15 megapascals (MPa; about 2,200 psi) when tested according to ASTM D-882 at room temperature and at 25 centimeters per minute, and the Young's modulus of the layer exceeds 2,000 MPa (about 300,000 psi). Other desirable properties are that the reinforcing layer be printable, i.e., retain ink printed on it, so that, for example, printed information can be included in the reinforced area of the diaper as instructions to a user, or as a brand identification; and have a degree of softness (such as indicated by a Taber stiffness measurement of less than about 5) to leave the diaper supple and comfortable.

A preferred material for the reinforcing layer is a polyolefin, preferably polypropylene, which may have either a matte or shiny (smooth) surface. Polypropylene may also be used in a biaxially oriented form. Polyethylene terephthalate film is another useful material as are other polyesters such as polybutylene terephthalate. The reinforcing layer typically has a thickness between about 10 and 75 micrometers.

The bonding layer of the bilayer reinforcing film should not adhere to the reinforcing layer when exposed for a typical period of time, e.g., a month or more, under possible storage conditions such as elevated temperatures (e.g., 50° C.) and elevated pressures as applied in a storage roll. However, the bonding layer must become adhered well to the reinforcing layer under certain conditions, e.g., at an elevated temperature such as used during extrusion or when solvent-cast against the reinforcing layer. Preferably, the bonding layer is extruded into direct and adhering contact with the reinforcing layer, either while the reinforcing layer is also being extruded or after the reinforcing layer is already formed. Typically, the bonding layer is between about 10 and 75 micrometers in thickness.

The bonding layer must also bond well to the liquid-impermeable outer film of the diaper through the application of heat and pressure. The bonding layer should hold the reinforcing layer to the diaper cover stock with greater force than that which is applied when the pressure-sensitive-adhesive fastening tape is adhered on the top surface of the reinforcing layer. To assure desired reinforcement, the bond should be sufficient to provide a peel strength (when peeled at 90° at a rate of 5 cm/minute) of at least 40 N/m, and preferably at least 200 N/m. Such a bond must be developed by application of heat at a temperature that avoids damage to the polyethylene film, i.e., avoiding any substantial wrinkling or other deformation of the film. Generally, the bonding layer softens to a tacky condition such that it will bond to the outer impermeable film of the diaper at temperatures of about 115° C.–120° C. or less, preferably 100° C. or less. To achieve good bonds, the bonding layer should generally have a surface energy lower than that of diaper cover stock, which for polyethylene films means that the bonding layer should have a surface energy of less than about 40 dynes per centimeter.

Good bonds also call for good cohesive strength in the bonding layer, which can generally be indicated by a tensile strength for the bonding layer of at least about one-half MPa, and preferably at least one MPa. To achieve needed cohesive strength, the bonding layer should generally include high-molecular-weight portions, e.g., portions having a molecular weight of at least 10,000 or preferably 20,000 in a proportion of at least 30% of the polymeric materials of the layer. Lower-molecular-weight portions such as low-molecular-weight fractions inherently included in a polymeric material during manufacture or low-molecular-weight polymers, copolymers, or resinous tackifiers blended into higher-molecular-weight portions reduce softening points to needed temperatures. Tackifiers are especially desirable in bonding layers of bilayer films of the invention because they increase tackiness at elevated temperatures of sealing, reduce surface energy, and increase adhesion to the diaper cover stock.

Figure 2:
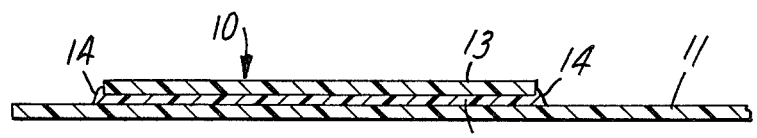
FIG. 2 is a cross-section view of a bilayer film of the invention bonded to diaper cover stock, taken along the lines 2—2 in FIG. 3.

Lower cohesive strength can be somewhat overcome by a characteristic achieved with some bilayer films of the invention illustrated in FIGS. 1 and 2. FIG. 1 is a perspective view of a representative bilayer film of the invention wound in a storage roll (showing the bilayer film in enlarged scale in the thickness dimension), and FIG. 2 is a cross-section through the reinforced fastening area of the outer impermeable film 11 of a diaper of the invention with the bilayer film 10 of FIG. 1 bonded to the film. With certain bilayer films of the invention in which the bonding layer exhibits a lower melt-viscosity, the bonding layer 12 of the bilayer film 10 flows during the bonding operation from the shape shown in FIG. 1 to the shape shown in FIG. 2. More specifically, as shown in FIG. 2, the bonding layer 12 flows to form a raised ridge 14 that surrounds the edge of the reinforcing layer 13, thereby making it more difficult for a person to pick at the bilayer film, or for an object to snag on it, to remove it.

We have obtained best results in achieving the combination of properties needed in the bonding layer through use of a blend of polymeric materials based on ethylene- and propylene-based copolymers, especially ethylene/vinyl acetate copolymers. For example, good results have been obtained with a blend of copolymers, one of which has a melt-flow index of 500 or more and another of which has a melt-flow index of 200 or less. Other useful materials for the bonding layer include synthetic rubbers or natural rubbers, generally together with a tackifying resin. For example, synthetic block copolymers such as styrene-butadiene block copolymers together with a tackifying resin and/or an endblock resin (a resin that is compatible primarily with the rigid block or phase of a synthetic block copolymer) such as coumarone-indene- or alpha-methylstyrene-based resins provide good results. Low-molecular-weight polyesters, low-molecular-weight polyester-polyamides and low-molecular-weight polyolefins also may be used.

Useful tackifying resins include petroleum-based hydrogenated hydrocarbon resins (often called C-9 resins, since they include monomeric molecular units that have nine carbon atoms), hydrogenated rosin esters, C-5 hydrocarbon resins, styrenated terpene resins, nonhydrogenated rosin esters, rosin acids, etc.

Other ingredients that may be included in the bonding layer besides the described polymeric ingredients are pigments, fillers, waxes (e.g., microcrystalline or paraffinic waxes), and antioxidants. The bilayer film of the invention typically has only two layers, but the term "bilayer" herein does not exclude the presence of other layers. For example, priming layers may be used between the structural and bonding layers.

The bilayer reinforcing film is preferably bonded to the surface of the diaper cover stock that forms the exterior surface of the diaper, but can also be adhered on the inner surface of the cover film, e.g., between the cover film and the absorbent pad of the diaper.

Figure 3:
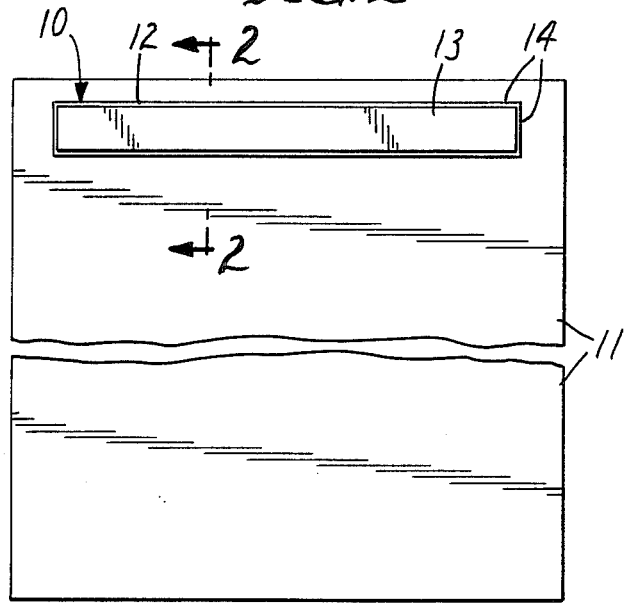
FIG. 3 is a top view of the diaper cover stock, or outer impermeable film of an individual diaper, with a reinforcing bilayer film of the invention bonded in place.

Typically, the bilayer reinforcing film is supplied in a roll, and lengths are cut from the roll and adhered to the outer or cover liquid-impermeable film of the individual diapers on a continuous manufacturing line for diapers. A length of the film is unwound from the roll, cut and laid against the liquid-impermeable film (on either its outer or inner surface) and pressed against the film with heat and pressure, as with a heated roll. A radiant heat source such as an infrared heat lamp can also be used as a heat source. Thereupon, the bonding layer softens and adheres to the film. As shown in FIG. 3, a disposable diaper and the outer liquid-impermeable film 11 of the diaper, is generally rectangular in shape, and the bilayer reinforcing film 10 is applied along one of the shorter side edges of the rectangle in a direction extending parallel to the short side. The applied bilayer reinforcing film may have various dimensions, but most generally will have a length and width, respectively, between 10 and 30 centimeters and 2.5 and 10 centimeters.

The invention will be further illustrated with the following examples. In all of the examples, the bilayer films described were successfully bonded to conventional 25-micrometer-thick polyethylene liquid-impermeable film in a heated platen press (Sentinel Heat Sealer) using a temperature of 200° F. (93° C.), a pressure of 90 psi (0.6 MPa), and a time of six seconds.

EXAMPLE 1

A polypropylene film about 45 micrometers in thickness (1.8 mil) and having matte surfaces on each side was hot-melt coated with a composition having the following formulation to prepare a bonding layer of about 38 micrometers thickness (1.5 mil).

TABLE I

| Ingredients | Percent by Weight |
| --- | --- |
| Random copolymer of ethylene and vinyl acetate having a melt-flow index of 2500 and a vinyl acetate content of 14 weight percent (Escorene MVO-2514, available from Exxon Chemical) | 80 |
| Random copolymer of ethylene and vinyl acetate having a melt-flow index of 88.1 and a vinyl acetate content of 46 weight percent (Elvax 46, available from duPont) | 10 |
| Petroleum-based hydrogenated hydrocarbon tackifying resin (Escorez 5380, available from Exxon Chemical) | 10 |

After the described bonding operation, the bilayer film was bonded to the polyethylene cover film with a 90° peel strength of 640 N/m.

EXAMPLE 2

Example 1 was repeated except that the bonding layer consisted only of the 2500-melt-flow-index random copolymer of ethylene and vinyl acetate (Escorene MVO-2514). Such a copolymer exhibits a tensile strength (tested as a 0.5 millimeter-thick film pressed from pellets of the resin in an Instron Tensile Tester) of 350 psi (2.41 MPa), a Young's modulus of 2900 psi (20 MPa), and a Ring and Ball softening point of 80° C. In the bonding operation, the bilayer film became bonded to the polyethylene film with a 90° peel strength of 360 N/m.

EXAMPLE 3

Polypropylene film having a thickness of about 45 micrometers and matte finishes on each surface was solution-coated with the formulation below to produce a bonding layer having a weight of about 3.5 milligrams per square centimeter.

TABLE II

| Ingredient | Parts by Weight |
| --- | --- |
| Styrene-butadiene block synthetic rubber having a styrene content of 30 weight percent (Finaprene 411, available from Fina Chemical Company) | 100 |
| Alpha-pinene terpene tackifying resin having a softening point of 135° C. (Piccolyte A135, available from Hercules Chemical Company) | 80 |
| d-limonene terpene tackifying resin having a softening point of 135° C. (Piccolyte C135, available from Hercules Chemical Company) | 80 |
| End-block reinforcing resin thought to be based on alpha-methyl styrene (Amoco 18-290, available from Amoco Chemical Company) | 10 |

The ingredients were dissolved in a 4:1 cyclohexane:methylene chloride solvent mixture to give a 25-weight-percent solids solution, the solution coated onto the polypropylene film, and the solvent evaporated. The resulting bilayer film became bonded to the polyethylene cover film with a 90° peel strength of 50 N/m.

EXAMPLE 4

Example 1 was repeated using a bonding layer composition having the following formulation.

TABLE III

| Ingredient | Percent by Weight |
| --- | --- |
| Random copolymer of ethylene and vinyl acetate having a melt-flow index of 148 and a vinyl acetate content of 18.5% by weight (Elvax 420, available from DuPont) | 70 |
| Random copolymer of ethylene and vinyl acetate having a melt-flow index of 2500 and a vinyl acetate content of 14 weight percent | 10 |
| Petroleum-based hydrogenated hydrocarbon tackifying resin (Escorez 5380, available from Exxon Chemical) | 20 |

This blend has a softening point of about 90° C. When the bilayer film was bonded to polyethylene diaper-cover stock in the described bonding operation, and an attempt made to peel away the bilayer film in the peel strength test, the pulling force on the bilayer film resulted in tearing of the polyethylene film rather than peeling away of the bilayer film.

EXAMPLE 5

Example 1 was repeated using a bonding composition having the following formulation.

TABLE IV

| Ingredient | Percent by Weight |
|---|---|
| Random copolymer of ethylene and vinyl acetate having a melt-flow index of 57 and a vinyl acetate content of 40 weight-percent (Elvax 40W) | 80 |
| Petroleum-based hydrogenated hydrocarbon tackifying resin (Escorez 5380) | 20 |

What is claimed is:

1. Disposable diaper which includes an outer liquid-impermeable film and a bilayer film bonded to the liquid-impermeable film as a peel-resistant reinforced fastening area to which pressure-sensitive adhesive fastening tapes attached at another part of the diaper may be adhaered to hold the diaper in a closed position, the bilayer film comprising a reinforcing layer and a room-temperature-nontacky bonding layer, and being bonded to the liquid-impermeable film under heat and pressure that leaves the liquid-impermeable film substantially undeformed, the bonding layer holding the reinforcing layer to the liquid-impermeable film with greater force than that which the fastening tape applies when adhered to the top of the bilayer film, whereby the fastending tapes may be reliably and lastingly adhered to the reinforced area of the diaper by hand pressure, and may be removed and reapplied, all without distortion or tearing of the liquid-impermeable film.

2. Diaper of claim 1 in which the bonding layer includes a tackifying resin.

3. Diaper of claim 1 in which the bonding layer comprises an ethylene/vinyl acetate copolymer.

4. Diaper of claim 2 in which the bonding layer comprises an ethylene/vinyl acetate copolymer.

5. Diaper of claim 3 in which the bonding layer comprises a blend of ethylene/vinyl acetate copolymers, one copolymer having a melt-flow index of at least 500 and another having a melt-flow index of no more than about 200.

6. Diaper of claim 4 in which the bonding layer comprises a blend of ethylene/vinyl acetate copolymers, one copolymer having a melt-flow index of at least 500 and another having a melt-flow index of no more than about 200.

7. Diaper of claim 1 in which the bonding layer has flowed so as to form a raised ridge surrounding the edge of the reinforcing layer.

8. Diaper of claim 1 in which the bilayer film is free of release treatments on its top surface.

9. Diaper of claim 1 in which the bilayer film is bonded to the liquid-impermeable film sufficiently to resist peeling from the liquid-impermeable film with a 90° peel strength of at least 200 N/m.

10. Diaper of claim 9 in which the bonding layer softens at a temperature less than 120° C.

11. Diaper of claim 10 in which the bonding layer is nontacky below 60° C.

12. Method for reinforcing the outer liquid-impermeable polyethylene film of a disposable diaper in an area to which pressure-sensitive-adhesive fastening tapes attached at another part of the diaper may be adhered to hold the diaper in a closed position, comprising bonding to the liquid-impermeable film a bilayer film that comprises a reinforcing layer and a room-temperature-nontacky bonding layer, the bilayer film being bonded to the liquid-impermeable film under heat and pressure that leaves the liquid-impermeable film substantially undeformed, and holding the reinforcing layer to the liquid-impermeable film with greater force than that which the pressure-sensitive adhesive of the fastening tape applies to the top of the bilayer film, whereby the free ends of the adhesive fastening tapes may be reliably and lastingly adhered to the reinforced area of the diaper by hand pressure, and may be removed and reapplied, all without distortion or tearing of the liquid-impermeable film.

13. Method of claim 12 in which the bonding layer includes a tackifying resin.

14. Method of claim 12 in which the bonding layer comprises an ethylene/vinyl acetate copolymer.

15. Method of claim 13 in which the bonding layer comprises an ethylene/vinyl acetate copolymer.

16. Method of claim 14 in which the bonding layer comprises a blend of ethylene/vinyl acetate copolymers, one copolymer having a melt-flow index of at least 500 and another having a melt-flow index of no more than about 200.

17. Method of claim 15 in which the bonding layer comprises a blend of ethylene/vinyl acetate copolymers, one copolymer having a melt-flow index of at least 500 and another having a melt-flow index of no more than about 200.

18. Method of claim 12 in which the bonding layer flows during the bonding operation so as to form a raised ridge surrounding the edge of the reinforcing layer.

19. Method of claim 12 in which the bilayer film is cut from a non-blocking storage roll, the bonding layer is nontacky at temperatures below about 60° C., has a tensile strength of at least about one-half MPa, and is bonded to the liquid-impermeable film at a temperature of less than about 120° C.

* * * * *

UNITED STATES PATENT AND TRADEMARK OFFICE
CERTIFICATE OF CORRECTION

PATENT NO.   :   4,710,190
DATED        :   December 1, 1987
INVENTOR(S)  :   Leigh E. Wood; John A. Miller; and Alan J. Sipinen It is certified that error appears in the above-identified patent and that said Letters Patent is hereby corrected as shown below:

Colume 7, line 17, "adhaered" should be -- adhered --.

Colume 7, line 27, "fastend-" should be -- fasten- --.

Signed and Sealed this

Twenty-seventh Day of September, 1988

*Attest:*

DONALD J. QUIGG

*Attesting Officer*   *Commissioner of Patents and Trademarks*